United States Patent [19]

Hofmann et al.

[11] 3,966,748

[45] June 29, 1976

[54] PARA-FLUOROPHENYL-N-HETEROCYCLIC SUBSTITUTED BUTANES

[75] Inventors: Corris Mabelle Hofmann, Ho-Ho-Kus; Sidney Robert Safir, River Edge, both of N.J.

[73] Assignee: American Cyanamid Company, Stamford, Conn.

[22] Filed: May 8, 1975

[21] Appl. No.: 575,846

[52] U.S. Cl............ 260/294.8 D; 260/293.72; 260/295 R; 260/296 R; 424/263; 424/267
[51] Int. Cl.². ........................................ C07D 213/34
[58] Field of Search ............... 260/294.8 D, 296 R, 260/295 R; 424/263

[56] References Cited
UNITED STATES PATENTS 3,598,829 8/1971 Bauer et al. ............... 260/294.8 D

*Primary Examiner*—Alan L. Rotman
*Attorney, Agent, or Firm*—Denis A. Polyn

[57] ABSTRACT

1-p-fluorophenyl-4-N-heterocyclic-1-butanols, 1-p-fluorophenyl-4-N-heterocyclic-1-butanol esters and p-fluoro-γ-heterocyclic butyrophenones having neuroleptic and analgesic activity.

16 Claims, No Drawings

PARA-FLUOROPHENYL-N-HETEROCYCLIC SUBSTITUTED BUTANES

BACKGROUND OF THE INVENTION

This invention resides in the field of 1-p-fluorophenyl-N-heterocyclic-substituted butanes useful as neuroleptic and analgesic agents, their preparation and use and compositions containing them. The compounds of this invention are prepared from the quaternary salt intermediates which form the subject matter of our concurrently filed and co-pending application Ser. No. 575,845, filed May 8, 1975, incorporated herein by reference.

SUMMARY OF THE INVENTION

This invention is concerned with 1-p-fluorophenyl-4-heterocyclic-1-butanols, esters thereof and p-fluoro-2-heterocyclic butyrophenones of the formula:

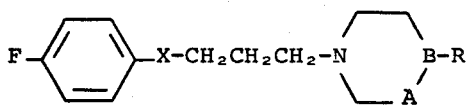

wherein X is selected from the group comprising

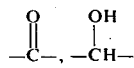

and

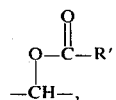

wherein R' is lower alkyl (preferably $C_1$–$C_6$); A—B is selected from the group comprising

and

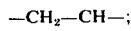

and R is selected from the group comprising:

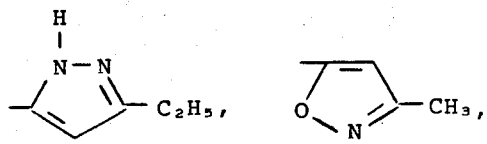 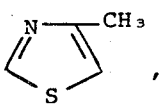

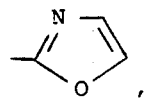 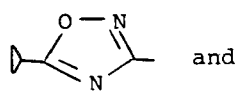 and 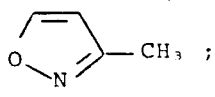

and the pharmaceutically acceptable acid addition salts thereof. Such compounds have been found to possess activity as anti-psychotic or neuroleptic and analgesic agents in animals.

This invention is also concerned with a method for the therapeutic management of manifestations of psychotic disorders, psychoneurotic conditions, anxiety, tension and pain in animals, especially warm-blooded animals, which comprises administering orally, parenterally or rectally to said animals an effective amount of the novel butanols, butyrophenones and esters of this invention sufficient to bring about relief. This invention is further concerned with therapeutic compositions containing the butanols, butyrophenones and esters in unit dosage form for having neuroleptic and analgesic activity in animals. This invention is still further concerned with a method for the preparation of the butanols, butyrophenones and esters of this invention from the quaternary salt intermediates.

Representative butanols encompassed within this invention include, for example, 3,6-dihydro-α-(p-fluorophenyl)-4-(3-methyl-5-isoxazolyl)-1(2H)-pyridinebutanol; 4-(5-cyclopropyl-1,2,4-oxadiazol-3-yl)-3,6-dihydro-α-(p-fluorophenyl)-1(2H)-pyridinebutanol; 3,6-dihydro-α-(p-fluorophenyl)-4-(4-methyl-2-thiazolyl)-1(2H)-pyridinebutanol; 3,6-dihydro-4-(3-ethyl-5-pyrazolyl)-α-(p-fluorophenyl)-1(2H)-pyridinebutanol; 3,6-dihydro-α-(p-fluorophenyl)-4-[5-(trifluoromethyl)-3-isoxazolyl]-1(2H)-pyridinebutanol; 3,6-dihydro-α-(p-fluorophenyl)-4-(2-oxazolyl)-1(2H)-pyridinebutanol; α-(p-fluorophenyl)-4-(4-methyl-2-thiazolyl)-1-piperidinebutanol; α-(p-fluorophenyl)-4-(2-oxazolyl)-1-piperidinebutanol; and 3,6-dihydro-4-(3-methyl-5-isoxazolyl)-α-phenyl-1(2H)-pyridinebutanol.

Representative butyrophenones encompassed within this invention include, for example, 4-[3,6-dihydro-4-(3-methyl-5-isoxazolyl)-1(2H)-pyridyl]-4'-fluoro-butyrophenone; 4-[4-(5-cyclopropyl-1,2,4-oxadiazol-3-yl)-3,6-dihydro-1(2H)-pyridyl]-4'-fluoro-butyrophenone; 4-[3,6-dihydro-4-(4-methyl-2-thiazolyl)-1(2H)-pyridyl]-4'-fluoro-butyrophenone; and 4-(3,6-dihydro-4-isoxazolyl-1(2H)-pyridyl)-4'-fluorobutyrophenone.

Representative esters encompassed within this invention include, for example, 3,6-dihydro-α-(p-fluorophenyl)-4-(3-methyl-5-isoxazolyl)-1(2H)-pyridinebutanol acetate, hydrochloride; 3,6-dihydro-α-(p-fluorophenyl)-4-(3-methyl-5-isoxazolyl)-1(2H)-pyridinebutanol propionate, hydrochloride; 3,6-dihydro-α-(p-fluorophenyl)-4-(2-oxazolyl)-1(2H)-pyridinebutanol acetate, hydrochloride; and 3,6-dihydro-α-(p-fluorophenyl)-4-(2-oxazolyl)-1(2H)-pyridinebutanol propionate, hydrochloride.

Typical quaternary salt intermediates useful in preparing the compounds of this invention include, for example, 4-(5-cyclopropyl-3-isoxazolyl)-1-(3-p-fluorobenzoylpropyl)pyridinium perchlorate; 4-(3-ethyl-5-pyrazolyl)-1-(3-p-fluorobenzoylpropyl)-pyridinium perchlorate; 4-(5-chloropropyl-1,2,4-oxadiazol-3-yl)-1-[3-(p-fluorobenzoyl)propyl]-pyridinium perchlorate; 1-(3-p-fluorobenzoylpropyl)-4-(4-methyl-2-thiazolyl)pyridinium chloride; 1-(3-p-fluorobenzoylpropyl)-4-(3-methyl-5-isoxazolyl)-pyridinium perchlorate; 4-(5-cyclopropyl-1,3,4-oxadiazol-2-yl)-1-(3-p-fluorobenzoylpropyl)-pyridinium perchlorate; 1-(3-(p-fluorobenzoylpropyl)-3-(4-methyl-2-thiazolyl)pyridinium perchlorate; 4-acetoacetyl-1-(3-p-fluorobenzoylpropyl)pyridinium chloride; 1-(3-p-fluorobenzoylpropyl)-4-[5-(trifluoromethyl)-3-isoxazolyl]pyridinium perchlorate; and 1-(3-p-fluorobenzoylpropyl)-4-(2-oxazolyl)-pyridinium perchlorate.

DETAILED DESCRIPTION OF THE INVENTION

The compounds of the present invention may be prepared as illustrated by the following reaction scheme, wherein R is as defined above and y is an anion of an acid.

The first step involves the preparation of the quaternary salt (III) from the γ-haloparafluorobutyrophenone (I) and 4-heterocyclicpyridine (II):

wherein halogen is chloro, bromo and iodo and in which I and II are heated together at about 80°–100°C. for about 18–24 hours. Ether or other appropriate solvent is added and the solid which separates is collected and dissolved in water. An acid such as perchloric acid, picric acid or chloroplatinic acid is added causing precipitation of the quaternary salt (III).

In the second step, the quaternary salt (III) of step 1 is dissolved in an alcoholic solvent, for example, methanol, ethanol or propanol and an alkali hydride reducing agent such as sodium borohydride, lithium aluminum hydride, or lithium ammonium hydride is added. After stirring for about 1–15 hours at about 25°–35°C., the solution is poured into water, and the unsaturated butanol IV which precipitates can be recrystallized from a suitable solvent such as acetonitrile, methanol or ethanol. This step may also be carried out by catalytic hydrogenation.

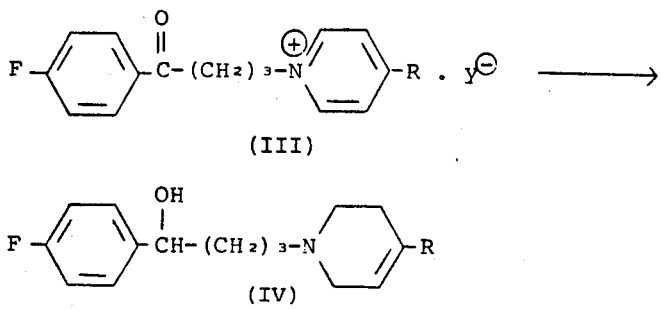

In the third step, the unsaturated butanol (IV) from step 2 is dissolved in acetic acid and a solution of a mild oxidizing agent such as chromic acid in acetic acid is added at 25°–30°C. After stirring for about 18–24 hours the solution is poured into water and neutralized with a mild base such as potassium carbonate. The butyrophenone (V) is extracted from the mixture with ether and recrystallized from a suitable solvent such as ethanol.

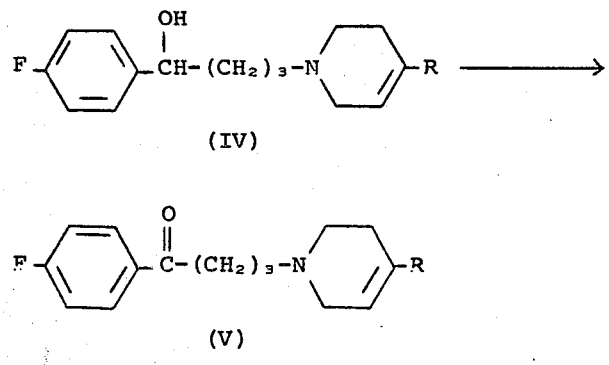

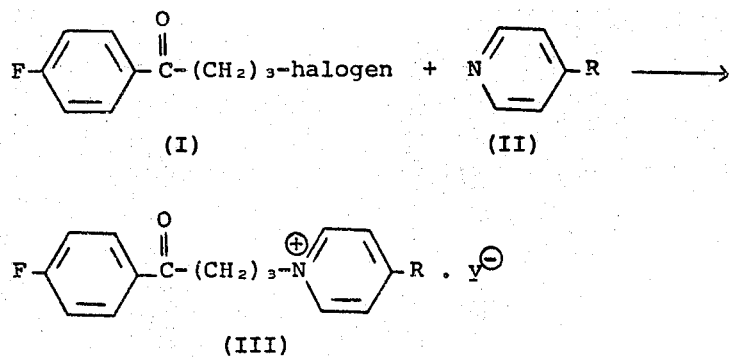

In the fourth step, the saturated butanol (VI) may be prepared from the unsaturated butanol (IV) by catalytic hydrogenation in a solvent such as ethanol using palladium on charcoal or other noble metal catalysts as the catalyst. After filtration of the mixture and evaporation of the solvent, the product (VI) is obtained as a crystalline solid.

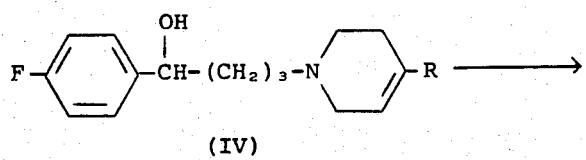

(IV)

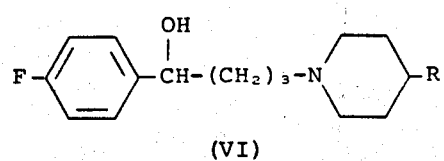

(VI)

In the fifth step, the unsaturated butanol (IV) is treated with stirring with a loweralkanoic anhydride such as acetic anhydride in the presence of a catalytic amount of a base such as pyridine or other basis amine, at 25°–30°C. for 18–24 hours. The mixture is evaporated to dryness at reduced pressure, and the residue is dissolved in ether and treated with a mineral acid such as hydrochloric acid to give the loweralkanoate ester as the mineral acid salt (VII).

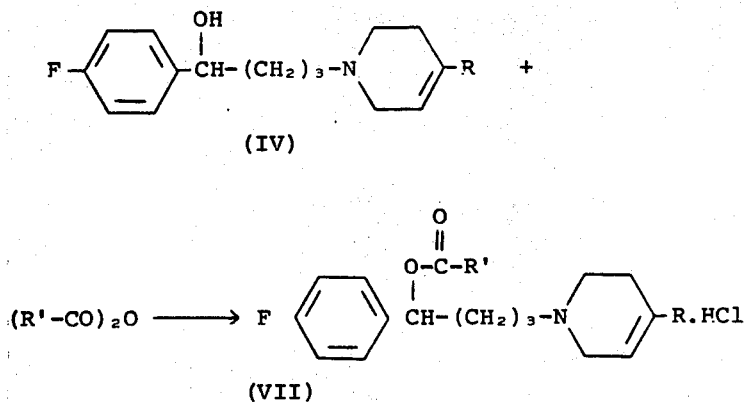

The compounds of this invention will be more fully illustrated by the following specific examples wherein Examples 1–9 illustrate the preparation of the quaternary salt intermediates and Examples 10-26, the butanols, butyrophenones and esters of this invention.

EXAMPLE 1

Preparation of 4-(5-Cyclopropyl-3-isoxazolyl)-1-(3-p-fluorobenzoylpropyl)pyridinium perchlorate A 1 g. portion of γ-chloro-p-fluorobutyrophenone and 0.9 g. of 4-(5-cyclopropyl-3-isoxazolyl)-pyridine are heated in an oil bath overnight at 100°C. Ether is added to the solid mass with stirring. The ether is decanted and the solid is recrystallized from acetonitrile. This oily solid is dissolved in water and perchloric acid is added. The resulting tan precipitate is recrystallized sequentially from methanol, ethanol and ethanol, melting point 139°–141.5°C.

EXAMPLE 2

Preparation of 4-(3-Ethyl-5-pyrazolyl)-1-(3-p-fluorobenzoylpropyl)-pyridinium perchlorate A 2.0 g. portion of γ-chloro-p-fluorobutyrophenone and 1.7 g. of 4-(3-ethyl-5-pyrazolyl)pyridine are heated in an oil bath for 5 hours at 100°C. and then cooled overnight. The solid is slurried in ether several times and recrystallized from acetonitrile. This solid is dissolved in water and perchloric acid is added causing precipitation of a solid. This solid is recrystallized three times from methanol, m.p. 55°–75°C. (gas bubbles).

EXAMPLE 3

Preparation of 4-(5-Cyclopropyl-1,2,4-oxadiazol-3-yl)-1-[3-(p-fluorobenzoyl)-propyl]pyridinium perchlorate A 1.0 g. portion of γ-chloro-p-fluorobutyrophenone and 0.9 g. of 4-(5-cyclopropyl-1,2,4-oxadiazol-3-yl)pyridine are heated in an oil bath at 100°C. overnight. The resulting oil is slurried several times with ether. The oil is added to water and the mixture is stirred and filtered. Perchloric acid is added to the filtrate causing formation of a tan solid. This solid is washed with water and recrystallized twice from methanol, m.p. 183°–184°C.

EXAMPLE 4

Preparation of 1-(3-p-Fluorobenzoylpropyl)-4-(4-methyl-2-thiazolyl)-pyridinium chloride A 1.0 g. portion of γ-chloro-p-fluorobutyrophenone and 0.9 g. of 4-(4-methyl-2-thiazolyl)pyridine are heated in an oil bath at 95°–100°C. overnight. Ether is added and the mixture is filtered. The solid is recrystallized from acetonitrile. This solid is recrystallized from a mixture of alcohol and ether, m.p. 226°–228°C.

EXAMPLE 5

Preparation of 1-(3-p-Fluorobenzoylpropyl)-4-(3-methyl-5-isoxazolyl)pyridinium perchlorate A 2.0 g. portion of γ-chloro-p-fluorobutyrophenone and 1.6 g. of 4-(3-methyl-5-isoxazolyl)pyridine are heated in an oil bath overnight at 100°C. The mixture is slurried with ether several times. The solid is recrystallized from 100 ml. of acetonitrile. This solid is dissolved in water, filtered and perchloric acid is added to the filtrate. The resulting solid is recrystallized twice from methanol, m.p. 135°–136.5°C.

EXAMPLE 6

Preparation of 4-(5-Cyclopropyl-1,3,4-oxadiazol-2-yl)-1-(3-p-fluorobenzoylpropyl)pyridinium perchlorate A 2.0 g. portion of γ-chloro-p-fluorobutyrophenone and 1.9 g. of 4-(5-cyclopropyl-1,3,4-oxadiazol-2-yl)pyridine are heated on a steam bath overnight. The mixture is slurried in ether and filtered. The resulting solid is recrystallized twice from ethanol. This solid is then recrystallized from acetonitrile yielding a solid (A). The filtrate on evaporation yields a solid (B) which is put on silica gel plates and extracted with methanol yielding a solid (C). Solids (A) and (C) are converted to the perchlorate, as previously described, combined and recrystallized from methanol, m.p. 168.5°–169°C.

EXAMPLE 7

Preparation of 1-(3-p-Fluorobenzoylpropyl)-3-(4-methyl-2-thiazolyl)-pyridinium perchlorate A 4.0 g. portion of γ-chloro-p-fluorobutyrophenone and 3.6 g. of 3-(4-methyl-2-thiazolyl)pyridine are heated on a steam bath overnight. The thick oil is slurried in ether several times until a tan solid is produced which is filtered and washed with ether. This solid is recrystallized from acetonitrile and then ethanol-ether, yielding a solid. The ethanol-ether mother liquor upon the addition of more ether yields an additional solid. The two solids are combined, converted to the perchlorate salt as previously described and recrystallized twice from methanol, m.p. 109°–110°C.

EXAMPLE 8

Preparation of 1-(3-p-Fluorobenzoylpropyl)-4-[5-(trifluoromethyl)-3-isoxazolyl]pyridinium perchlorate A 2.0 g. portion of γ-chloro-p-fluorobutyrophenone and 2.1 g. of 4-(5-trifluoromethyl-3-isoxazolyl)pyridine are heated on a steam bath overnight. The dark oil is slurried in ether several times and filtered. The brown solid is dissolved in water filtered and the filtrate is acidified with perchloric acid yielding a white solid. The solid is recrystallized twice from methanol, m.p. 64°–66°C.

EXAMPLE 9

Preparation of 1-(3-p-Fluorobenzoylpropyl)-4-(2-oxazolyl)-pyridinium perchlorate A 2.0 g. portion of γ-chloro-p-fluorobutyrophenone and 1.5 g. of 4-(2-oxazolyl)pyridine are heated on a steam bath overnight. The mixture is slurried in ether several times and filtered giving a dark solid which is recrystallized from acetonitrile, dissolved in water and filtered. The filtrate is acidified with perchloric acid, yielding a tan solid. This solid is recrystallized twice from methanol, m.p. 162°–163.5°C.

EXAMPLE 10

Preparation of 3,6-Dihydro-α-(p-fluorophenyl)-4-(3-methyl-5-isoxazolyl)pyridinebutanol To a 1.7 g. portion of 1-(3-p-fluorobenzoylpropyl)-4-(3-methyl-5-isoxazolyl)pyridinium perchlorate, prepared as described in Example 5, in 80 ml. of methanol is added 1.6 g. of sodium borohydride, portionwise with stirring. This mixture is stirred at room temperature for 2 hours. The mixture is evaporated to about one-half volume and poured into 150 ml. of cold water. The white solid which forms is recrystallized from aqueous ethanol, m.p. 116°–119°C.

EXAMPLE 11

Preparation of 4-(5-Cyclopropyl-1,2,4-oxadiazol-3-yl)-3,6-dihydro-α-(p-fluorophenyl)-1(2H)-pyridinebutanol To a 1.8 g. portion of 4-(5-cyclopropyl-1,2,4-oxadiazol-3-yl)-1-[3-(p-fluorobenzoyl)-propyl]-pyridinium perchlorate, prepared as described in Example 3, in 80 ml. of methanol is added, portionwise with stirring, 1.8 g. of sodium borohydride. The mixture is stirred for 2 hours and then poured into 300 ml. of cold water, causing a white solid to separate. This solid is collected and recrystallized from acetonitrile, m.p. 89°–92°C.

EXAMPLE 12

Preparation of 3,6-Dihydro-α-(p-fluorophenyl)-4-(4-methyl-2-thiazolyl)-1(2H)-pyridinebutanol To a 0.4 g. portion of 1-(3-p-fluorobenzoylpropyl)-4-(4-methyl-2-thiazolyl)pyridinium chloride, prepared as described in Example 4, in 20 ml. of methanol is added portionwise with stirring 0.4 g. of sodium borohydride. The mixture is stirred for 2 hours and then poured into water causing the formation of a white solid which is separated and recrystallized from acetone and water, m.p. 89°–90.5°C.

EXAMPLE 13

Preparation of 3,6-Dihydro-4-(3-ethyl-5-pyrazolyl)-α-(p-fluorophenyl)-1(2H)-pyridinebutanol To a 2.2 g. portion of 4-(3-ethyl-5-pyrazolyl)-1-(3-p-fluorobenzoylpropyl)pyridinium perchlorate, prepared as described in Example 2, in 100 ml. of methanol is added portionwise with stirring 2.2 g. of sodium borohydride. The mixture is stirred for 2 hours and then poured into ice water causing formation of a white solid which was collected and recrystallized from methanol, m.p. 140.5°–141.5°C.

EXAMPLE 14

Preparation of
3,6-Dihydro-α-(p-fluorophenyl)-4-[5-(trifluoromethyl)-3-isoxazolyl]-1(2H)-pyridinebutanol To a 1.0 g. portion of 1-(3-p-fluorobenzoylpropyl)-4-[5-(trifluoromethyl)-3-isoxazolyl]pyridinium perchlorate, prepared as described in Example 8, in 40 ml. of methanol, is added portionwise with stirring 1.0 g. of sodium borohydride. The mixture is stirred for 2 hours and poured into ice-water causing the formation of a white solid which is collected and recrystallized from methanol, m.p. 120.5°–121.5°C.

EXAMPLE 15

Preparation of
3,6-Dihydro-α-(p-fluorophenyl)-4-(2-oxazolyl)-1(2H)-pyridinebutanol To a 1.75 g. portion of 1-(3-p-fluorobenzoylpropyl)-4-(2-oxazolyl)pyridinium perchlorate, prepared as described in Example 9, in 75 ml. of methanol, is added portionwise with stirring 1.75 g. of sodium borohydride. The mixture is stirred for 1½ hours, allowed to stand, some of the methanol is evaporated and the mixture is poured into ice water causing the formation of a tan solid which is recovered by filtration, m.p. 100°–103°C.

EXAMPLE 16

Preparation of
α-(p-Fluorophenyl)-4-(4-methyl-2-thiazolyl)-1-piperidinebutanol

A 0.35 g. portion of 3,6-dihydro-α-(p-fluorophenyl)-4-(4-methyl-2-thiazolyl)-1(2H)-pyridinebutanol, prepared as described in Example 12, is dissolved in 10 ml. of ethanol and 0.1 g. of palladium on carbon catalyst is added. The mixture is reduced to room temperature and pressure for about 26 hours. The mixture is filtered and the filtrate evaporated yielding a white solid which is recrystallized from acetonitrile giving a white crystalline solid, m.p. 98°–99°C.

EXAMPLE 17

Preparation of
α-(p-Fluorophenyl)-4-(2-oxazolyl)-1-piperidinebutanol

A 0.32 g. portion of 3,6-dihydro-α-(p-fluorophenyl)-4-(2-oxazolyl)-1(2H)-pyridinebutanol, prepared as described in Example 15, is dissolved in 10 ml. of ethanol and 0.1 g. of palladium on carbon catalyst is added. The mixture is reduced at room temperature and pressure for 4 hours and then filtered. The filtrate is evaporated giving an oil which solidifies to a white solid. This solid is recrystallized twice from acetonitrile, m.p. 99°–100°C.

EXAMPLE 18

Preparation of
3,6-Dihydro-4-(3-methyl-5-isoxazolyl)-α-phenyl-1(2H)-pyridinebutanol To a 4.1 g. portion of 1-(3-benzoylpropyl)-4-(3-methyl-5-isoxazolyl)pyridinium perchlorate [prepared by the reaction of γ-chlorobutyrophenone and 4-(3-methyl-5-isoxazolyl)pyridine as described in the previous examples] in 200 ml. of methanol is added, portionwise with stirring, 4.1 g. of sodium borohydride. The mixture is allowed to stand at room temperature overnight, evaporated to about 1/2 volume and poured into ice water. The white solid is collected and recrystallized from acetonitrile, m.p. 108°–109°C.

EXAMPLE 19

Preparation of
4-[3,6-Dihydro-4-(3-methyl-5-isoxazolyl)-1(2H)-pyridyl]-4'-fluoro-butyrophenone A 1.65 g. portion of 3,6-dihydro-α-(p-fluorophenyl)-4(3-methyl-5-isoxazolyl)-1(2H)-pyridine butanol, prepared as described in Example 10, in 35 ml. of acetic acid is stirred at room temperature. A 30 ml. portion of chromic acid in acetic acid (prepared by dissolving 1.1 gm of chromium oxide in 50 ml. of acetic acid and 10 ml. of water) is added dropwise and the mixture is stirred for 3 hours and then allowed to stand overnight. A few drops of methanol are added and sufficient solid sodium bicarbonate to neutralize the solution. Water is also added. The mixture is extracted 3 times with ether. The extracts are dried over magnesium sulfate, filtered and evaporated yielding a pink solid which is recrystallized twice from methanol, m.p. 96°–98°C.

EXAMPLE 20

Preparation of
4-[4-(5-Cyclopropyl-1,2,4-oxadiazol-3yl)-3,6-dihydro-1(2H)-pyridyl]-4'-fluoro-butyrophenone A 0.36 g. portion of 4-(5-cyclopropyl-1,2,4-oxadiazol-3-yl)-3,6-dihydro-α-(p-flurophenyl)-1(2H)-pyridinebutanol, prepared as described in Example 11, in 10 ml. of acetic acid is stirred at room temperature. A 6 ml. portion of chromic acid in acetic acid solution is added dropwise. The mixture is stirred for 2 hours and then allowed to stand overnight. A few drops of methanol and some water is added and the solution is neutralized with solid sodium bicarbonate. The mixture is extracted 3 times with ether. The extracts are dried over magnesium sulfate, filtered and evaporated, yielding a white solid which is recrystallized from aqueous methanol, m.p. 67°–68°C.

EXAMPLE 21

Preparation of
4-[3,6-Dihydro-4-(4-methyl-2-thiazolyl)-1(2H)-pyridyl]-4'-fluoro-butyrophenone A 1.4 g. portion of 3,6-dihydro-α-(p-fluorophenyl)-4-(4-methyl-2-thiazolyl)-1(2H)-pyridinebutanol, prepared as described in Example 12, in 30 ml. of acetic acid is stirred at room temperature. A 24 ml. portion of chromic acid in acetic acid is added dropwise. The mixture is stirred for 3 hours and then allowed to stand overnight. The mixture is poured onto ice water and neutralized with sodium carbonate. The mixture is extracted 3 times with ether. The extracts are dried over magnesium sulfate, filtered and evaporated, giving an oil which solidifies. This solid is recrystallized twice from aqueous methanol yielding a tan solid, m.p. 81°–82°C.

EXAMPLE 22

Preparation of 4-(3,6-Dihydro-4-isoxazolyl-1(2H)-pyridyl)-4'-fluorobutyrophenone A 1.58 g. portion of 3,6-dihydro-α-(p-fluorophenyl)-4-(2-oxazolyl)-1(2H)-pyridinebutanol, prepared as described in Example 15, in 45 ml. of acetic acid is stirred at room temperature. A 30 ml. portion of chromic acid in acetic acid is added dropwise. The mixture is stirred for 2 hours and allowed to stand overnight. A few drops of methanol are added, the mixture is poured into ice water and neutralized with sodium carbonate. The mixture is extracted with ether. The ether extract is dried over magnesium sulfate, filtered and evaporated yielding an oil which solidifies. This solid is dissolved in ether, alcoholic HCl is added and the mixture is filtered. The solid is slurried in acetone, filtered and recrystallized twice from ethanol, m.p. 178°–178.5°C.

EXAMPLE 23

Preparation of 3,6-Dihydro-α-(p-fluorophenyl)-4-(3-methyl-5-isoxazolyl)-1(2H)-pyridinebutanol acetate, hydrochloride A one gram portion of 3,6-dihydro-α-(p-fluorophenyl)-4-(3-methyl-5-isoxazolyl)-1(2H)-pyridinebutanol prepared as described in Example 10, in 6 ml. of acetic anhydride and 2 drops of pyridine is stirred at room temperature for about 1 hour. The clear solution, after standing for 18–20 hours is evaporated to dryness. The residue is dissolved in ether and treated with 2.5N alcoholic hydrogen chloride solution to give a white solid. One recrystallization from methanol-ether gives a white crystalline solid, m.p. 156.5°–157°C dec.

EXAMPLE 24

Preparation of 3,6-Dihydro-α-(p-fluorophenyl)-4-(3-methyl-5-isoxazolyl)-1(2H)-pyridinebutanol propionate, hydrochloride A 1 gram portion of 3,6-dihydro-α-(p-fluorophenyl)-4-(3-methyl-5-isoxazolyl)-1(2H)-pyridinebutanol prepared as described in Example 10, is treated with 6 ml. of propionic anyhydride and pyridine in the same manner as described in Example 23. The product is obtained as a white crystalline solid, m.p. 164.5°–165.5°C. dec.

EXAMPLE 25

Preparation of 3,4-Dihydro-α-(p-fluorophenyl)-4-(2-oxazolyl)-1(2H)-pyridinebutanol acetate, hydrochloride A 1.3 g. portion of 3,6-dihydro-α-(p-fluorophenyl)-4-(2-oxazolyl)-1(2H)-pyridinebutanol, prepared as described in Example 15, in 8 ml. of acetic anhydride and 2 drops of pyridine is stirred at room temperature for 18–20 hours and then evaporated to dryness. The residue is dissolved in ether and treated with 2.5N alcoholic hydrogen chloride solution. The solid which separates is recrystallized from methanol-ether to give a white crystalline solid, m.p. 176°–176.5°C.

EXAMPLE 26

Preparation of 3,4-Dihydro-α-(p-fluorophenyl)-4-(2-oxazolyl)-1(2H)-pyridinebutanol propionate, hydrochloride A mixture of 2.6 g. of 3,6-dihydro-α-(p-fluorophenyl)-4-(2-oxazolyl)-1(2H)-pyridinebutanol, prepared as described in Example 15, 16 ml. of propionic anhydride and 2 drops of pyridine is stirred at room temperature for 18–20 hours and then evaporated to dryness. The residue is dissolved in ether and treated with 2.5N alcoholic hydrogen chloride. The sticky solid which separates is recrystallized from isopropyl alcohol to give a white crystalline solid, m.p. 164°–165°C.

The butanols, butyrophenones and esters of this invention are physiologically active on the central nervous system and possess antipsychotic (neuroleptic or tranquilizing) properties as shown by their ability to decrease locomotor activity in warm-blooded animals. Groups of four rats are treated orally with the compound dissolved or suspended in starch vehicle at the maximum tolerated dose. At the estimated time of peak effect, animals are placed singly into an Animex Activity Counter and the activity of each rat is recorded for a 5 minute period. The activity counts are compared to historical or parallel control values to determine significant decreased locomoter activity. The compound is considered an active depressant if the counts are 50% or less of control values. The median effective doses (doses which decrease locomotor activity by 50%) are determined in groups of six rats for those compounds deemed active, by a method of least squares (D. F. Finney, Statistical Methods in Biological Assay, Second Edition, Hofner Publishing Co., New York, 456–457, 1964). The median effective dose for several compounds of the present invention are recorded in Table I.

Table I

| Compound | $MDD_{50}$ (mg/Kg) |
|---|---|
| 4[3,6-Dihydro-4-(3-methyl-5-isoxazolyl)-1(2H)-pyridyl]-4-fluorobutyrophenone | 11.2 |
| 4[4-(5-Cyclopropyl-1,2,4-oxadiazol-3-yl)-3,6-dihydro-1(2H)-pyridyl]-4'-fluorobutyrophenone | 22.3 |
| 3,6-Dihydro-4-(3-ethyl-5-pyrazolyl)-α-(p-fluorophenyl)-1(2H)-pyridinebutanol | 8.6 |

The ability of the butanols, butyrophenones and esters of this invention to decrease locomotor activity in mice is measured by means of an actophotometer (a photoelectric device for quantitatively measuring locomotor activity). Graded doses of the active compounds prepared by the processes of this invention are administered to groups of five mice, and the effective dosage range for a significant reduction of motor activity compared to control groups is established. The use of reduced motor activity as a measure of tranquilizing activity has been described by W. D. Gray, A. C. Osterberg, and C. E. Rauh, Archives Internationales et de Therapie, Vol. 134, p. 198 (1961) and W. J. Kinnard and C. J. Carr, Journal of Pharmacology and Experimental Therapeutics, Vol. 121, p. 354 (1957). The effective dose that causes a 50% reduction in motor activity (MDD₅₀) expresses in milligrams per kilogram of body weight, of some typical compounds of the present invention is set forth in Table II.

Table II

| Compound | MDD₅₀ (mg/Kg) |
|---|---|
| 3,6-Dihydro-α-(p-fluorophenyl)-4-(3-methyl-5-isoxazolyl)-1(2H)-pyridinebutanol | 7 |
| 4-[3,6-Dihydro-4-(3-methyl-5-isoxazolyl)-1(2H)-pyridyl]-4'-fluorobutyrophenone | 26 |
| 3,6-Dihydro-α-(p-fluorophenyl)-4-(4-methyl-2-thiazolyl)-1(2H)-pyridinebutanol | 0.24 |
| 3,6-Dihydro-4-(3-ethyl-5-pyrazolyl)-α-(p-fluorophenyl)-1(2H)-pyridinebutanol | 9.4 |
| 4-[3,6-Dihydro-4-(4-methyl-2-thiazolyl)-1(2H)-pyridyl]-4'-fluorobutyrophenone | 1.5 |
| 3,6-Dihydro-α-(p-fluorophenyl)-4-(2-oxazolyl)-1(2H)-pyridinebutanol | 2 |
| α-(p-Fluorophenyl)-4-(4-methyl-2-thiazolyl)-1-piperidinebutanol | 2 |
| 4-(3,6-Dihydro-4-isoxazolyl-1(2H)-pyridyl)-4'-fluorobutyrophenone | 2.5 |

The butanols, butyrophenones and esters of the present invention are active analgesics when measured by the "writhing syndrome" test for analgesic activity as described by Siegmund, et al., Proc. Soc. Exp. Bio. and Med., 95, 729 (1957), with modifications. This method is based upon the reduction of the number of writhes following the intraperitoneal injection of one mg./kg. of body weight of phenyl-p-quinone in male Swiss albino mice weighing 18–25 gm. The syndrome is characterized by intermittent contractions of the abdomen, twisting and turning of the trunk, and extension of the hind legs beginning 3 to 5 minutes after injection of the phenyl-p-quinone. The test compounds are administered orally at the indicated dose to groups of two mice each, 30 minutes before injection of the phenyl-p-quinone. The total number of writhes exhibited by each group of mice is recorded for a 3 minute period commencing 15 minutes after injection of the phenyl-p-quinone. A compound is considered active if it reduces the total number of writhes in two test mice from a control value of approximately 30 per pair to a value of 18 or less. Table III summarizes the results of this test on representative compounds of this invention.

Table III

| Compound | Dose mg/Kg | No. of writhes per pair |
|---|---|---|
| 3,6-Dihydro-α-(p-fluorophenyl)-4-(3-methyl-5-isoxazolyl)-1(2H)-pyridinebutanol | 100 | 3, 0 |
| 4-[3,6-Dihydro-4-(3-methyl-5-isoxazolyl)-1(2H)-pyridyl]-4'-fluoro-butyrophenone | 100 | 2, 0 |
| 4-(5-Cyclopropyl-1,2,4-oxadiazol-3-yl)-3,6-dihydro-α-(p-fluorophenyl)-1(2H)-pyridinebutanol | 200 | 0, 7 |
| 4-[4-(5-Cyclopropyl-1,2,4-oxadiazol-3-yl)-3,6-dihydro-1(2H)-pyridyl]-4'-fluoro-butyrophenone | 200 | 0, 0 |
| 3,6-Dihydro-4-(3-ethyl-5-pyrazolyl)-α-(p-fluorophenyl)-1(2H)-pyridinebutanol | 25 | 5, 2 |
| 4-[3,6-Dihydro-4-(4-methyl-2-thiazolyl)-1(2H)-pyridyl]-4'-fluoro-butyrophenone | 25 | 0, 0 |
| α-(p-Fluorophenyl)-4-(4-methyl-2-thiazolyl)-1-piperidinebutanol | 100 | 0, 6 |
| α-(p-Fluorophenyl)-4-(2-oxazolyl)-1-piperidinebutanol | 100 | 0, 0 |
| 4-(3,6-Dihydro-4-isoxazolyl-1(2H)-pyridyl)-4'-fluoro-butyrophenone | 6.25 | 2, 3 |

Another test used to determine analgesic activity for the compounds of this invention is a modification of the method of Randall and Selitto [Arch. Int. Pharmacodyn., 111, 409 (1957)]. This test measures the pain threshold of rats whose paws are made sensitive to pressure by the injection of a 20% aqueous suspension (0.1 ml.) of brewers' yeast into the plantar surface of the left hind paw. Constantly increasing force (16 grams/second) is applied to the swollen paw using an Analgesy Meter, Ugo Basile. The pressure is cut off at 250 grams of force when there is no response (sudden struggle or vocalization). Control rats treated with the starch vehicle respond to a pressure or force of about 30 grams. Pressure-pain thresholds are always recorded two hours after administration of brewers' yeast. Analgesic agents are administered at the same time as the yeast, at the maximum tolerated dose (MRD) orally. Ratios of treated (T)/controls (C) reaction thresholds are calculated as estimates of analgesic efficacy (degree of analgesia attainable). A compound is accepted as active when the T/C ratio is greater than 1.36. Table IV gives the results obtained with representative compounds.

Table IV

| Compound | MTD | Ratio (treated/control) measured 2 hrs. following oral dosing |
|---|---|---|
| 3,6-Dihydro-4-(3-ethyl-5-pyrazolyl)-α-(p-fluorophenyl)-1(2H)-pyridinebutanol | 12.5 | 1.47 |
| 3,6-Dihydro-α-(p-fluorophenyl)-4-(3-methyl-5-isoxazolyl)-1(2H)-pyridinebutanol | 12.5 | 1.41 |
| α1(p-Fluorophenyl)-4-(2-oxazolyl)-1-piperidinebutanol | 100 | 1.64; 1.40 |
| 3,6-Dihydro-α-(p-fluorophenyl)-4-(3-methyl-5-isoxazolyl)-1(2H)-pyridinebutanol acetate, hydrochloride | 6.25 | 1.51 |
| 3,6-Dihydro-α-(p-fluorophenyl)-4-(3-methyl-5-isoxazolyl)-1(2H)-pyridinebutanol | 100 | 2.28(1.81) |

Table IV-continued

| Compound | MTD | Ratio (treated/control) measured 2 hrs. following oral dosing |
|---|---|---|
| propionate, hydrochloride | | |

The butanols, butyrophenones and esters of this invention serve as neroleptic or analgesic agents in doses of about 0.5 mg. per kg. to about 50 mg. per kg. of body weight per day. A preferred dosage regimen would be from about 2 mg. per kg. to about 29 mg. per kg. of body weight per day. When such dosage units are employed, a total daily intake of a subject of about 70 kg. body weight is about 35 mg. to about 3.5 g., preferably about 140 mg. to about 2.0 g.

For therapeutic administration, the active compounds of this invention may be given orally, parenterally, rectally or the like and incorporated with excipients and used, for example, in the form of tablets, dragees, capsules, suppositories, liquids, elixirs, emulsions, suspensions, syrups, chocolate, candy, wafers, chewing gum, solutions for parenteral administration or the like. Such compositions and preparations should contain at least 0.1% of active compound. The percentage in the compositions and preparations may, of course, be varied, and may conveniently be between about 2% and 60% or more of the weight of the unit. The amount of active compound in such therapeutically useful compositions or preparations is such that a suitable dosage will be obtained. This dosage can also be obtained by the use of sustained release preparations. Preferred compositions or preparations according to the present invention are prepared so that a dosage unit form contains between about 1 and about 250 milligrams of the active compound of this invention.

Tablets, pills, dragees, and the like, may contain the following: a binder such as gum tragacanth, acacia, corn starch, or gelatin; a disintegrating agent such as corn starch, potato starch, alginic acid, or the like; a lubricant such as stearic acid, magnesium stearate, talc, or the like; a sweetening agent such as sucaryl or saccharin may be added, as well as a flavoring such as peppermint, oil of wintergreen or cherry flavoring. In addition, the active ingredients may be incorporated into sustained release preparations. Preparations of this type would contain greater quantities of the active ingredients.

The active compounds of this invention may be administered parenterally. Butanols, butyrophenones and esters having the desired clarity, stability, and adaptability for parenteral use are obtained by dissolving the active compound in a vehicle consisting of a polyhydric aliphatic alcohol or mixtures thereof. Especially satisfactory are glycerin, propylene glycol, and the polyethylene glycols. The polyethylene glycols consist of a mixture of non-volatile, normally liquid, polyethylene glycols which are soluble in both water and organic liquids and which have molecular weights of from about 200 to about 1500. While concentrations can vary greatly, the amount of active compound dissolved in the above vehicle preferably should be from about 0.01 to about 10.0% by weight. Although various mixtures of the aforementioned non-volatile polyethylene glycols may be employed, it is preferred to use a mixture having an average molecular weight of from about 200 to about 400.

In addition to the active compounds, the parenteral solutions of the present invention may also contain various preservatives which may be used to prevent bacterial and fungal contamination. The preservatives which may be used for such purpose are, for example, benzyl alcohol, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, ascorbic acid, sodium bisulfite, sodium metabisulfite, and sodium formaldehyde sulfoxylate. Generally, from about 0.05 to about 0.2% concentrations of antioxidant are employed.

We claim:
1. A compound of the formula:

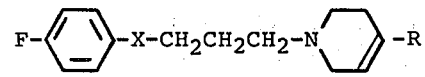

wherein X is selected from the group consisting of

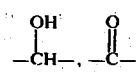

and

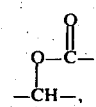

wherein R' is lower alkyl; and R is selected from the group consisting of:

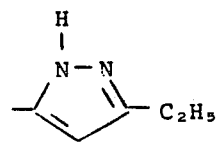 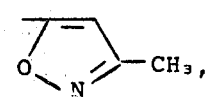 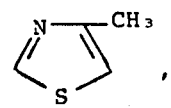

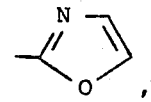 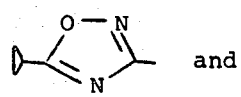 and 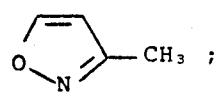

and pharmaceutically acceptable acid addition salts thereof.

2. A compound according to claim 1, 3,6-dihydro-α-(p-fluorophenyl)-4-(3-methyl-5-isoxazolyl)-pyridinebutanol.

3. A compound according to claim 1, 4-(5-cyclopropyl-1,2,4-oxadiazol-3-yl)-3,6-dihydro-α-(p-fluorophenyl)-1(2H)-pyridinebutanol.

4. A compound according to claim 1, 3,6-dihydro-α-(p-fluorophenyl)-4-(4-methyl-2-thiazolyl)-1(2H)-pyridinebutanol.

5. A compound according to claim 1, 3,6-dihydro-4-(3-ethyl-5-pyrazolyl)-α-(p-fluorophenyl)-1(2H)-pyridinebutanol.

6. A compound according to claim 1, 3,6-dihydro-α-(p-fluorophenyl)-4-[5-(trifluoromethyl)-3-isoxazolyl]-1(2H)-pyridinebutanol.

7. A compound according to claim 1, 3,6-dihydro-α-(p-fluorophenyl)-4-(2-oxazolyl)-1(2H)-pyridinebutanol.

8. A compound according to claim 1, 3,6-dihydro-4-(3-methyl-5-isoxazolyl)-α-phenyl-1(2H)-pyridinebutanol.

9. A compound according to claim 1, 4-[3,6-dihydro-4-(3-methyl-5-isoxazolyl)-1(2H)-pyridyl]-4'-fluorobutyrophenone.

10. A compound according to claim 1, 4-[4-(5-cyclopropyl-1,2,4-oxadiazol-3-yl)-3,6-dihydro-1(2H)-pyridyl]-4'-fluoro-butyrophenone.

11. A compound according to claim 1, 4-[3,6-dihydro-4-(4-methyl-2-thiazolyl)-1(2H)-pyridyl]-4'-fluoro-butyrophenone.

12. A compound according to claim 1, 4-(3,6-dihydro-4-isoxazolyl-1(2H)-pyridyl)-4'-fluoro-butyrophenone.

13. A compound according to claim 1, 3,6-dihydro-α-(p-fluorophenyl)-4-(3-methyl-5-isoxazolyl)-1(2H)-pyridinebutanol acetate, hydrochloride.

14. A compound according to claim 1, 3,6-dihydro-α-(p-fluorophenyl)-4-(3-methyl-5-isoxazolyl)-1(2H)-pyridinebutanol propionate, hydrochloride.

15. A compound according to claim 1, 3,6-dihydro-α-(p-fluorophenyl)-4-(2-oxazolyl)-1(2H)-pyridinebutanol acetate, hydrochloride.

16. A compond according to claim 1, 3,6-dihydro-α-(p-fluorophenyl)-4-(2-oxazolyl)-1(2H)-pyridinebutanol propionate, hydrochloride.

* * * * *